United States Patent

Patru

[11] 4,039,312
[45] Aug. 2, 1977

[54] BACTERIOSTATIC, FUNGISTATIC AND ALGICIDAL COMPOSITIONS, PARTICULARLY FOR SUBMARINE PAINTS

[76] Inventor: Marcel Joseph Gaston Patru, 60 Sainte-Eusoy, Froissy, France

[21] Appl. No.: 541,129

[22] Filed: Jan. 15, 1975

Related U.S. Application Data

[63] Continuation-in-part of Ser. No. 372,608, June 22, 1973, abandoned.

[30] Foreign Application Priority Data

July 4, 1972 France .................. 72.24127

[51] Int. Cl.² ............................ A01N 11/00
[52] U.S. Cl. ........................ 71/67; 424/148; 424/245; 424/152; 106/15 R
[58] Field of Search ........... 424/148, 184, 245; 71/67

[56] References Cited

U.S. PATENT DOCUMENTS

| | | | |
|---|---|---|---|
| 2,909,459 | 10/1959 | Hovey | 424/148 |
| 3,027,371 | 3/1962 | Starrs | 260/270 |
| 3,455,976 | 7/1969 | Wade | 210/429.3 |
| 3,492,328 | 1/1970 | Kotzsch | 260/448.8 |

OTHER PUBLICATIONS

Merck Index, 7th Ed. (1960), pp. 841, 845.
Chemical Abstracts, vol. 74 (1971), p. 73232q.

Primary Examiner—V. D. Turner
Attorney, Agent, or Firm—Eric P. Schellin

[57] ABSTRACT

This invention relates to bacteriostatic, fungistatic and algicidal compositions.

Said compositions comprise a metal derivative of N-hydroxypyridinethione of the formula:

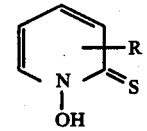

in which R represents a hydrogen atom, a lower alkyl radical, a lower alkoxy radical or a halogenated lower alkyl radical, together with a compound selected from the haloborates and the halosilicates.

3 Claims, No Drawings

BACTERIOSTATIC, FUNGISTATIC AND ALGICIDAL COMPOSITIONS, PARTICULARLY FOR SUBMARINE PAINTS

This is a Continuation-in-Part of the U.S. patent application No. 372,608 filed on June 22, 1973 and now abandoned.

This invention relates to compositions for the control of microorganisms. More particularly, it relates to bacteriostatic, fungistatic and algicidal compositions, and especially compositions for submarine paints.

The problem of the fouling of the hulls of ships by various organisms (bacteriae, fungi, algae, molluscs) has not yet received entirely satisfactory solutions.

The prevention method which has been found the most efficient heretofore is based on the introduction of one or more toxic substances in the coating material or in the paint protecting the hulls of ships.

Thus, copper salts or copper derivatives, generally cuprous oxide alone or in combination with other toxic materials such as mercuric oxide, or yet other combinations more toxic to the forms of animal life such as mercury and organomercury derivatives in combination with copper or arsenic derivatives have been used.

Said materials, to be efficient, should be introduced in large amounts in the coatings and, thus, their very high toxicity is apparent on the marine life in the vicinity of ships. In addition, said toxicity is actually unsafe for the workers who apply the paint or the coating.

It has also been suggested to use organotin salts which are found to be more active, but which have the same drawbacks from the standpoint of toxicity.

It is also known that the metal derivatives of N-hydroxypyridinethiones of the formula:

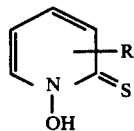

(I)

in which R represents a hydrogen atom, a lower alkyl radical, a lower alkoxy radical or a halogenated lower alkyl radical possess bacteriostatic and fungistatic properties (see U.S. Pat. No. 2,686,786 and French Patent No. 1,209,013). Said derivatives have low toxicity but they have insufficient activity to be used in submarine paints, for example.

Applicant has found that the haloborates and halosilicates enhance the bacteriostatic and fungistatic properties of the metal derivatives of N-hydroxypyridenthiones and that compositions containing a metal derivative of N-hydroxypyridinethione and a haloborate or a halosilicate possess algicidal properties.

Thus, this invention has for its object to provide a composition comprising a metal derivative of a N-hydroxypyridinethione of the above-mentioned type and a compound selected from the haloborates and the halosilicates.

While possessing a strong bacteriostatic, fungistatic and algicidal activity, the compositions of this invention have low toxicity for humans and the higher animals.

Said properties and the comparatively low cost of said compositions make them particularly advantageous for a large number of applications.

The preferred compositions are those which contain fluoborates or fluosilicates as haloborates or halosilicates.

The activity of the compositions of this invention was evidenced in vitro and compared with that of a N-hydroxypyridinethione salt used alone.

Tests were carried out in tubes containing dilute agar-agar, with the following compositions:

A— Zinc salt of N-hydroxypyridinethione: 100% by weight

B — Zinc salt of N-hydroxypyridinethione: 10% by weight
Potassium fluoborate: 90% by weight C — Zinc salt of N-hydroxypyridinethione: 10% by weight
Sodium fluosilicate: 90% by weight The spectra of antibacterial and antifungal activity are given in the following Tables:

SPECTRA OF ANTIBACTERIAL ACTIVITY

Minimum inhibitory concentration expressed as micrograms H.P.T.Zn/ milliliter of solution

| Microorganisms | A | B | C |
|---|---|---|---|
| Staphilococcus aureus | 0.6 | 0.04 | 0.04 |
| Klebsiella pneumoniae | 2.4 | 0.08 | 0.08 |
| B.C.G., bovine variety | 0.06 | 0.02 | 0.02 |
| Pseudonomas aeruginosa | 6.3 | 0.8 | 0.4 |
| Escherichia coli | 2.4 | 0.2 | 0.12 |

SPECTRA OF ANTIFUNGAL ACTIVITY

Minimum inhibitory concentration expressed as micrograms H.P.T.Zn/milliliter of solution

| Microorganisms | A | B | C |
|---|---|---|---|
| Aspergillus niger | 6 | 0.8 | 0.8 |
| Trichophyton mentagrophytes | 3 | 0.4 | 0.4 |
| Penicillium notatum | 3 | 0.2 | 0.2 |
| Candida albicans | 3 | 0.4 | 0.2 |
| Saccharaomyces cerevisiae | 3 | 0.4 | 0.4 |

The synergistic effect obtained from the combination of a metal derivative of N-hydroxypyridinethione with a haloborate or halosilicate is apparent from said Tables.

The combination of this invention is predominantly useful in paints and most particularly as anti-fouling component in anti-fouling paints. It shoud be noted that the combination may be added to any paint composition, whether consisting of an anhydrous system or of an aqueous dispersion. The combination, which is highly biostatic, imparts this property to any paint, proportionally to the amounts added. It may be added, in particular to paints, as a pigment or as a dispersible concentrate.

The present invention provides also compositions comprising a bacteriostatically and fungistatically effective amount of the combination of this invention.

Satisfactory activity is generally obtained when the metal derivative of N-hydroxypyridinethione and the haloborate or the halosilicate are used in a weight ratio within the range from 1:1 to 1:100, depending on the intended use.

The compositions of this invention may be used not only in paints, but also as anti-slime material in the white papermaking waters, to inhibit the flora which develops in the water-cooling circuits, in drilling muds, in jet fuel, in the ponds used for handling nuclear materials or in cutting and machining fluids for metals, or also to conduct antibacterial and antifungal treatments on textiles or plastics.

Depending on the applications, more or less water-soluble salts may be used. Thus, in paints, it is preferred to use salts which are sparingly water-soluble or water-insoluble, particularly a zinc or zirconium salt of a N-hydroxypyridinethione of the formula (I) in combination with potassium fluoborate or an ammonium, calcium, potassium or sodium fluosilicate. In the applications where the combination according to the invention is in the form of an aqueous solution, it is preferred to use an alkali-metal salt of a N-hydroxypyridinethione of the formula (I) in combination with a sodium, barium, zinc, tin or ammonium fluoborate or with an aluminum, barium, magnesium, lead or zinc fluosilicate.

The N-hydroxypyridinethione and haloborate or halosilicate content in the medium in which they are dispersed or dissolved may be varied within a large range, depending on the applications.

Thus, in the case of paints, the combination according to the invention comprises from 0.3 to 15% and preferably from 0.8 to 3.6% by weight of the total composition. For other applications, said levels may be much lower. Thus, for cooling circuits, from 1 to 10 ppm of the combination of this invention may be used, while 50 ppm of this combination may be used advantageously in jet fuels.

The following examples illustrate the invention without, however, limiting same.

EXAMPLE 1

One part by weight of zinc N-hydroxypyridinethione roughly admixed with ten parts potassium fluoborate are introduced into a dry milling device (such as a hammer-mill, a ball-mill, and the like) and the mixture is then ground.

EXAMPLE 2

The procedure described in Example 1 is used, except that the 10 parts of potassium fluoborate are reduced to 5 parts per 1 part of zinc N-hydroxypyridinethione.

EXAMPLE 3

The procedure described in Example 1 is used, except that the potassium fluoborate is substituted with sodium fluosilicate.

The powders obtained in Examples 1, 2 and 3 may be directly incorporated in a paint during its manufacture, in the manner of a pigment or a filler.

EXAMPLE 4

Zinc N-hydroxypyridinethione (30 g), potassium fluoborate (300 g) and a non-ionic surface-active agent (nonylphenol condensed with 9 moles ethylene oxide) (150 g) are mixed in a mixing device.

A 50:50 mixtue of water and monoethylene glycol (520 g) is then added thereto. The mixture is homogenized and is then ground in a colloid mill, in a three-cylinder mill or in a ball-mill, to give 1 kg of concentrated paste which may suitably be added to any paint.

EXAMPLE 5

The procedure of Example 4 is used, except that the 30 g of zinc salt are substituted with 60 g of the same zinc salt.

EXAMPLE 6

The procedure of Example 4 is used, except that the fluoborate is substituted with sodium fluosilicate.

The concentrates obtained in Examples 4–6 are immediately dispersible, merely with stirring, in paint compositions which are hydrophobic or in the form of an emulsion.

EXAMPLE 7

The following paint composition, useful as "interior" tropical paint, is prepared by milling, to give a particle size of 40 microns.

| Materials | Parts, by weight |
|---|---|
| Acrylic emulsion | 22.00 |
| Titanium dioxide | 14.00 |
| Barium sulfate | 12.00 |
| Kaolin | 2.00 |
| Calcium carbonate | 22.20 |
| Diatomaceous silica | 2.00 |
| Carboxy methyl cellulose | 1.00 |
| Water | 20.00 |
| Sodium hydroxide (5% solution) | 1.00 |
| Anti-foaming solution | 1.00 |
| Diethylene glycol | 1.80 |
| Zinc N-hydroxypyridinethione/potassium fluoborate (1:2) | 100 |
| | 100.00 |

EXAMPLE 8

The following paint composition, useful as "exterior" tropical paint, is prepared according to the procedure of Example 7.

| Materials | Parts, by weight |
|---|---|
| Rutile titanium dioxide | 18.00 |
| Calcium carbonate | 20.00 |
| Mica | 6.00 |
| Diatomaceous silica | 6.00 |
| Vinyl toluene-butadiene copolymer resin | 6.00 |
| Styrene-acrylic copolymer resin | 0.70 |
| Chlorinated paraffin (40%) | 3.30 |
| Chlorinated paraffin (70%) | 3.30 |
| Hexyl epoxy stearate | 0.70 |
| White spirit (Kauri-Butanol index = 36/40) | 34.00 |
| Zinc N-hydroxypyridinethione/Potassium fluoborate (1:2) | 2.00 |
| | 100.00 |

EXAMPLE 9

A swimming-pool paint composition (comprising chlorinated rubber) is prepared according to the procedure of Example 7.

| Materials | Parts, by weight |
|---|---|
| Chlorinated rubber | 18 |
| Chlorinated paraffin (containing 48% chlorine) | |
| Rutile titanium dioxide | 18 |
| Zinc N-hydroxypyridinethione/Potassium fluoborate | 2 |
| Toluene | 30 |
| White-spirit | 20 |
| | 100 |

EXAMPLES 10, 11 and 12

Paint compositions similar to those of Examples 7, 8 and 9 are prepared by substituting the potassium fluoborate with sodium fluosilicate used in the same proportions.

EXAMPLE 13

Anti-fouling paint compositions formulated as set forth in following Tables I and II are prepared by ball-milling to give a maximum particle size of 40 microns after milling.

The formulations set forth in Table I (references 100, 101, 102 and 103) are consistent with U.S. Government Paint Specifications (New Specifications Supplement Feb. 3, 1952, 52-MC-403b Paint Ship-Bottom, Antifouling). Parts are by weight.

The formulations set forth in Table II (references 200, 201, 202) are merchant marine type standard sub-marine paint compositions consistent with French Specifications. Parts are by weight.

TABLE I

| Components | Control formulation Reference 101 | Toxicant-free formulation Reference 100 | Control formulation with T.B.T.F. Reference 102 | Formulation according to this invention Reference 103 |
|---|---|---|---|---|
| Zinc oxide powder | 14.50 | 14.50 | 14.50 | 14.50 |
| Red iron oxide | 5.50 | 6.95 | 5.50 | 5.50 |
| Red cuprous oxide | 28.80 | 28.80 | 26.25 | 27.55 |
| Magnesium silicate | 5.50 | 5.50 | 5.50 | 5.50 |
| Mercuric oxide | 1.45 | — | — | — |
| Tributyltin fluoride | — | — | 4.00 | — |
| Claimed composition | — | — | — | 2.70 |
| Rosin WW | 17.65 | 17.65 | 17.65 | 17.65 |
| Pine oil | 2.80 | 2.80 | 2.80 | 2.80 |
| Coal tar (80% non volatiles) | 5.50 | 5.50 | 5.50 | 5.50 |
| Naphtha solvent 90/180 | 9.15 | 9.15 | 9.15 | 9.15 |
| Petroleum spirits | 9.15 | 9.15 | 9.15 | 9.15 |
|  | 100.00 | 100.00 | 100.00 | 100.00 |

TABLE II

| Materials | Toxicant-free control formulation Reference 200 | Control formulation with tributyltin fluoride Reference 201 | Test formulation with claimed composition Reference 202 |
|---|---|---|---|
| Red cuprous oxide | 25.60 | 25.60 | 25.60 |
| Red iron oxide | 13.30 | 9.30 | 10.60 |
| Zinc oxide powder | 2.85 | 2.85 | 2.85 |
| Tributyltin fluoride | — | 4.00 | — |
| Claimed composition | — | — | 2.70 |
| Methanol | 0.50 | 0.50 | 0.50 |
| Bentonite | 0.50 | 0.50 | 0.50 |
| Linseed fatty acid | 0.95 | 0.95 | 0.95 |
| Lecithine | 0.95 | 0.95 | 0.95 |
| Hydrogenated castor oil | 1.70 | 1.70 | 1.70 |
| Rosin WG | 18.50 | 18.50 | 18.50 |
| Soft coumarone | 6.15 | 6.15 | 6.15 |
| Naphtha solvent 90/180 | 29.00 | 29.00 | 29.00 |
|  | 100.00 | 100.00 | 100.00 |

Various compositions according to references 103 and 202 were prepared, in which the biostatic combination was as follows:

Table III

| Biostatic composition | Formula |
|---|---|
| A | Zinc N-hydroxypyridinethione |
| B | Potassium fluoborate |
| C | Sodium fluosilicate |
| D | Zinc N-hydroxypyridinethione/potassium fluoborate in a 1:2 ratio |
| E | Zinc N-hydroxypyridinethione/sodium fluosilicate in a 1:2 ratio |

Fouling tests were conducted with these various paints on panels immersed under rafts in Le Havre harbor.

Two successive layers of the anti-fouling paints were applied on sand blasted, solvent-treated and dried soft steel panels previously coated with 1 layer of wash primer and 3 layers of anti-corrosion paint. The average thickness of each antifouling paint (after drying) was about 40 microns, i.e., an average total thickness of antifouling paint of 80 microns.

The panels were removed from the water and examined at 3 month intervals. The presence of molluscs, green algae, bryozoae, serpulae and the like was noted on control glass panels. After a period of time of 15 months, the weight of fouling organisms on such control panels was found to be 14.8 kg/m2. The results obtained in such tests are set forth in tabular form in Table IV, in which the percentages indicate the Fouled surface/Total surface ratio for each panel.

TABLE IV

| References | Percent after 3 months | 6 months | 9 months | 12 months | 15 months |
|---|---|---|---|---|---|
| 100 | 0 | 40% | 100% | — | — |
| 101 | 0 | 0 | 0 | 5% | 30% |
| 102 | 0 | 0 | 0 | 5% | 40% |
| 103A | 0 | 15% | 100% | — | — |
| 103B | 0 | 20% | 100% | — | — |
| 103C | 0 | 15% | 100% | — | — |
| 103D | 0 | 0 | 0 | 5% | 15% |

TABLE IV-continued

| References | Percent after | 3 months | 6 months | 9 months | 12 months | 15 months |
|---|---|---|---|---|---|---|
| 103E | | 0 | 0 | 0 | 5% | 30% |
| | 200 | 0 | 40% | 100% | — | — |
| | 201 | 0 | 0 | 0 | 10% | 45% |
| | 202A | 0 | 10% | 100% | — | — |
| | 202B | 0 | 25% | 100% | — | — |
| | 202C | 0 | 25% | 100% | — | — |
| | 202D | 0 | 0 | 0 | 5% | 20% |
| | 202E | 0 | 0 | 0 | 10% | 35% |

It is apparent from such results that the components of the combination according to the invention possess an anti-fouling activity which is much lower than that of the combination and that they may not be used alone as antifouling components.

The compositions of this invention have an efficiency which is equal or superior to that of the usual toxicants (mercuric oxide, tributyltin fluoride) which exhibit a much higher toxicity in Man.

Other fouling tests were conducted with submarine paints containing a combination according to this invention and with paints containing an anti-fouling material, tributyl tin fluoride, which is considered at the present time as the most active material in this field:

Various amounts of the composition obtained in Example 2 were added to the same paint as disclosed in Example 13 under reference 200 (standard submarine paint, of merchant marine type), to give paints A, B and C containing 1.2%, 2.4% and 3.6%, respectively, of the combination of this invention with respect to the weight of ready-to-use paint. For comparative purposes, a paint of same type containing 4% tributyl tin fluoride was used.

Thoroughly cleaned and degreased test panels were given two successive coatings of each test paint, on their front and back sides; Immediately after drying, they were immersed facing South (one side facing South and, therefore, one side facing North).

The final examinations were made after the panels had been immersed for a period of time of 12 months.

The following data were obtained on examination of the side facing South:

| | |
|---|---|
| Control (tributyl tin fluoride) | Non-adhesvie biologic veil |
| | Some non-adhesive algae |
| Paint A (1.2%) | Slight non-adhesive biologic veil |
| | Some non-adhesive algae |
| Paint B (2.4%) | Very slight non-adhesive biologic veil |
| | Some non-adhesive algae |
| Paint C (3.6%) | No biologic veil |
| | Some non-adhesive algae |

On the side facing North: no development.

All the above data relate to tests carried out in the Mediterranean area (Marseilles harbour) in a dock having an intense biology.

Tests carried out in the Channel area (Le Havre harbour) showed no change during the same period of time.

It is therefore apparent that, at a concentration of 1.2%, the combination of this invention exhibits an activity substantially equal to that of tributyl tin fluoride at a concentration of 4%. Moreover, considering that submarine paints are generally applied with a gun, the use of the combinations of this invention is found to be highly preferable to that of tributyl tin fluoride which has a much higher toxicity.

Having now described my invention what I claim as new and desire to secure by Letters Patent is:

1. A composition having bacteriostatic, fungistatic and algicidal properties comprising a zinc salt of a N-hydroxypyridinethione having the formula

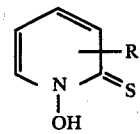

in which R is selected from the group consisting of hydrogen, lower alkyl, lower alkoxy and halogenated lower alkyl, and a fluorinated compound selected from the group consisting of potassium fluoborate and sodium fluosilicate, wherein the zinc salt and the fluorinated compound are present in a weight ratio of 1:2 to 1:10.

2. The composition as claimed in claim 1 comprising zinc N-hydroxypyridinethione and potassium fluoborate in a weight ratio of 1:2 to 1:10.

3. The composition as claimed in claim 1 comprising zinc N-hydroxypyridinethione and sodium fluosilicate in a weight ratio of 1:2 to 1:10.

* * * * *